United States Patent [19]

Speier

[11] 4,064,155
[45] Dec. 20, 1977

[54] PREPARATION OF SILYLAMINE HYDROCHLORIDES

[75] Inventor: John L. Speier, Midland, Mich.

[73] Assignee: Dow Corning Corporation, Midland, Mich.

[21] Appl. No.: 643,222

[22] Filed: Dec. 22, 1975

[51] Int. Cl.$^2$ .............................. C07F 7/10; C07F 7/18
[52] U.S. Cl. .............................................. 260/448.8 R
[58] Field of Search ................................ 260/448.8 R

[56] References Cited

U.S. PATENT DOCUMENTS

| 2,972,598 | 2/1961 | Morehouse | 260/448.8 R X |
| 3,557,178 | 1/1971 | Gölitz et al. | 260/448.8 R |
| 3,560,543 | 2/1971 | Plueddemann | 260/448.8 R X |

OTHER PUBLICATIONS

Noll, "Chemistry and Technology of Silicones", Academic Press, N.Y. (1968), p. 174.

*Primary Examiner* — Paul F. Shaver
*Attorney, Agent, or Firm* — Robert F. Fleming, Jr.

[57] ABSTRACT

Silylamine hydrochlorides are prepared by reacting a silane of the formula $(RO)_nR'_{3-n}SiR''Cl$ with at least two moles of an amine and thereafter volatilizing the amine to obtain a hydrochloride of the formula $(RO)_nR'_{3-n}SiR''NR'''_2 \cdot HCl$.

11 Claims, No Drawings

PREPARATION OF SILYLAMINE HYDROCHLORIDES

BACKGROUND OF THE INVENTION

It is well known that amine salts can be prepared by reacting the free amine with the appropriate acid. Amine salts of various alkenyl functional aminosilanes are shown in U.S. Pat. No. 3,819,675. These are made by the reaction of silyl alkyl halides such as $(CH_3O)_3SiRCl$ with unsaturated amines or with aminosilanes such as $(CH_3O)_3SiRNH_2CH_2CH_2NH_2$ and unsaturated halides such as vinylbenzyl chloride. According to this patent the ratio of halide to amine is about 1:1 to 1.5:1, and the excess amine is not volatilized after the reaction.

It is also known from U.S. Pat. No. 3,650,814 that silanes of the formula $XR'SiY_3$ where X can be amino or their hydrolyzates can be applied to glass to increase the adhesion of organic plastics. One of the silanes disclosed is $HCl.H_2NCH_2CH_2NH(CH_2)_3Si(OCH_3)_3$. However, this patent does not show how such salts are prepared nor that the "hydrolyzates" disclosed therein are water soluble.

It is the object of this invention to provide a novel more economical method for preparing organosilylamine hydrochlorides in which the unreacted amine is volatilized from the reaction zone after the reaction has been completed and particularly to provide such a method in which the products form stable concentrated water solutions.

DESCRIPTION OF THE INVENTION

This invention relates to a process for preparing the hydrochloride salt of a silyl(alkyl)amine which comprises reacting (1) a silane of the formula $(RO)_nR'_{3-n}SiR''Cl$ with at least two moles of (2) a compound of the group $R'''_2NH$ and $HR'''NCH_2CH_2NR'''_2$ to form (3) $\{(RO)_nR'_{3-n}SiR''\}_mNR'''_{3-m}$, $(RO)_nR'_{3-n}SiR''NR'''CH_2CH_2NR'''_2$ and $\{(RO)_nR'_{3-n}SiR''NR'''CH_{2-}\}_2$ in which (3) has a boiling point higher than (2) and thereafter removing (2) from the reaction zone by volatilization whereby compounds of the formulae $\}(RO)_nR'_{3-n}SiR''\}_mNR'''_{3-m}.HCl$. $(RO)_nR'_{3-n}SiR''NR'''CH_2CH_2NR'''_2.HCl$ and $\{(RO)_nR'_{3-n}SiR''NR'''CH_2-\}_2.2HCl$ are obtained in which R is an alkyl or an alkoxyalkyl radical of from 1 to 4 carbon atoms,
n is 2 to 3,
R' is a lower alkyl radical,
R'' is an alkylene radical of 1 to 4 carbon atoms,
R''' is hydrogen or an alkyl radical of 1 to 8 carbon atoms, and
m is 1 or 2.

Thus, it can be seen that the process produces the hydrochlorides of monosilyl alkyl amines having one silicon atom per molecule and di(silylalkyl) amines having two silicon atoms per molecule. Usually a mixture of the two is obtained unless (2) has only one active hydrogen, e.g. $(CH_3)_2NH$ or $(CH_3)_2NCH_2CH_2N(CH_3)H$ in which case a disilyl alkyl amine is not formed. In order to produce products which form stable solutions in water at concentrations of 15 percent by weight or higher, the amount of disilyl alkyl amine hydrochloride in the product should be not more than 30 mole percent (preferably not more than 12 mole percent) of the total product. That is, the ratio of monosilyl alkyl amine salt to disilyl alkyl amine salt should be at least 2 to 1 and preferably at least 7 to 1.

This invention also relates to water solutions made by dispersing in water the amine hydrochlorides defined above which hydrochlorides contain no more than 30 mole percent (preferbly 12 mole percent) disilyl alkyl amine hydrochloride. When the mixture contains more disilyl alkyl amine salt than this, the solutions are not stable on storage.

It should be understood that the utility of the products made by the claimed process is not restricted to water soluble compounds. Those products not water soluble are soluble in organic solvents such as alcohols. Organic solvent solutions can be used in coupling applications as well as aqueous solutions. However, in this day of ecological problems aqueous solutions are preferred.

As stated above there should be at least two moles of (2) per mole of (1). In order to obtain stable aqueous solutions in those cases where (2) is ammonia, or a diamine containing at least two active hydrogens, the ratio of (2) to (1) should be at least 12:1 and 3:1 respectively. Thus, less than 30 mole percent disilyl alkyl amine is obtained in the product when primary or secondary amines are used in amount at least two moles per mole of (1), when diamines containing at least two active hydrogens are used in amount of at least three moles per mole of (1) and when ammonia is used in amount of at least 12 moles per mole of (1). Unreacted (2) can be recycled if desired.

The aqueous solutions are obtained by dispersing the salts in water at which time the alkoxy groups hydrolyze to generate corresponding alcohols. If desired, alcohols can be removed by distillation in which case less toxic, less flammable and even more stable solutions are obtained. It should be understood, however, the aqueous solutions claimed herein include those which contain hydrolyzed alcohol and those from which the alcohol has been removed.

The pressure used in reacting (1) with (2) is not critical but where (2) is ammonia or a volatile amine the reaction is normally run under autogenous pressure. The temperature is not critical but excellent results are obtained in the range from 50° to 150° C.

If desired the reaction can be carried out in the presence of polar solvents such as lower aliphatic alcohols such as methanol, ethanol, isopropanol or the monomethyl ether of ethylene glycol. Whereas the presence of such solvents is not critical for the instant reaction, they are often desirable in order to lessen the chance of phase separation in the reacting mixture and to increase the yield of monosilyl alkyl amines.

When the silyl chloride in β-chloroethyl, protonated material such as water or alcohols should be avoided in order to prevent cleavage of the β-chloroethyl group. After the reaction with the amine has occurred, the resulting amine or an amine hydrochloride is stable to cleavage.

The reactants (1) of this invention can be any chloroalkyl silicon alkoxides of the defined type such as chloromethyldimethoxyethoxysilane, chloromethylmethyldimethoxysilane, α-chloroethylethyldiethoxysilane, 3-chloropropyltriisopropoxysilane, 3-chlorobutyltrimethoxysilane, 3-chloropropylpropyldimethoxysilane and 3-chloropropyltris-β-methoxyethoxysilane. Thus, it can be seen that R can be the same or different in any one molecule. It is preferred that R' have 1 to 4 carbon atoms.

Reactants (2) employed in this invention can be ammonia or any lower aliphatic monoamine such as methyl amine, dimethyl amine, ethylmethyl amine, ethyl amine, isopropyl amine, butyl amine, or octyl amine and diamines such as ethylenediamine, N-methylethylene diamines, N,N-dimethylethylenediamine and N,N,N'-trimethylethylenediamine. Thus, it can be seen that the amines can be primary or secondary and the substituent on the nitrogen can be the same or different groups. It is preferred but not essential that the amine employed boil below 150° C. at atmospheric pressure. However, the only critical feature is that the amine (2) boil below the boiling point of (3).

The amine salts of this invention (both the water soluble and organic solvent soluble forms) are useful as coupling agents between inorganic substrates and organic plastics. The amine salts can be employed either by treating the substrate and then applying the plastic or by adding the salts to the plastic before mixing with the inorganic material. Preferably, the substrate is treated with a solution containing from 0.1 to 1 percent by weight of the amine salts, dried and thereafter mixed with the plastic and the composite is then molded. The salts can be applied from an organic solvent solution, from an aqueous solution or neat.

Since water is the cheapest of all solvents and causes no ecological problems, it is advantageous to store concentrated solutions made by dispersing the amine salts in water, until they are need at which time the concentrated solutions are diluted to the desired degree and applied to the substrates. The preferred compositions of this invention (e.g., those containing less than 30 mole percent and preferably less than 12 mole percent di(silylalkyl) amine salts are stable in water at 15 to 50 or more percent by weight concentration and these solutions can be kept without gellation which makes such solutions very useful compositions of commerce.

The materials of this invention can be used on inorganic substrates such as glass, clay, silica or metals. The resins which can be used with the products of this invention are the well-known commercial systems such as epoxies, phenolics, polyesters, polyolefins and the like.

The following examples are illustrative only and should not be construed as limiting the invention which is properly delineated in the appended claims.

EXAMPLE 1

Twelve moles of ammonia, 500 ml. of methanol and 1.2 moles of 3-chloropropyltrimethoxysilane were heated to 100° C. for 16 hours in a 3 liter stainless steel autoclave. The product was then heated at 95° C. at 50 mm. mercury to remove volatile substances leaving behind the residue that solidified at room temperature to a wax-like, crystalline material. A portion of the product was dissolved in methanol and titrated with sodium methoxide and the resulting material analyzed by gas chromatography. Analytical results showed that the product was a mixture of $(CH_3O)_3Si(CH_2)_3NH_2.HCl$ and $\{(CH_3O)_3Si(CH_2)_3\}_2NH.HCl$ in the mole ratio of 2.1:1. The mixture was water soluble but the solution was stable on storage only at a concentration of 15.5 percent by weight or less in water.

EXAMPLE 2

7.1 moles of methyl amine, 500 ml. of methanol and 1.42 moles of 3-chloropropyl trimethoxy silane were heated at 100° C. for 3 hours in an autoclave. The product was then heated at 95° C. at 50 mm. mercury to remove the excess amine and methanol. A liquid residue was obtained which was 99 percent yield of a mixture of the salts $(CH_3O)_3Si(CH_2)_3NH(CH_3).HCl$ and $\{(MeO)_3Si(CH_2)_3\}_2NH.HCl$ in a ratio of approximately 140:1.

The mixture readily dissolved in water at room temperature to give a stable, low viscosity 50 percent by weight solution having a viscosity of 13 cps. which has remained unchanged in a sealed glass bottle for 1 year.

EXAMPLE 3

4.39 moles of n-butyl amine, 200 ml. of methanol and 0.877 moles of 3-chloropropyltrimethoxysilane were heated to reflux (75° C.) for 18 hours. The solution was then heated to 200° C. at atmospheric pressure to remove volatile substances. The residue solidified at room temperature to form a semi-crystalline, white product which was shown to be 99 percent of the salt $(CH_3O)_3Si(CH_2)_3NHC_4H_9.HCl$. The product was soluble in water and readily soluble in methanol.

EXAMPLE 4

7 moles of 3-chloropropyltrimethoxy silane, 29.8 moles of ethylene diamine and 315 g. of methanol were heated to 100° C. when the solution began to reflux spontaneously from an exothermic reaction. The temperature rose to 117° C. during several minutes of vigorous refluxing. As soon as the refluxing subsided, volatile materials were removed as the product was heated to 150° C. and the pressure slowly reduced to 20 mm. of mercury. A clear liquid residue remained which was 96.5 percent yield calculated as $(CH_3O)_3Si(CH_2)_3NHCH_2CH_2NH_2.HCl$. The product became a semi-crystalline mass at room temperature.

Solution A — A portion of this mass was easily dissolved in water to give a 50 percent by weight solution. The solution had a base neutral equivalent of 439, calculated 444. A portion of this solution was heated to remove methanol formed by hydrolysis and additional water was added to make a 50 percent by weight solution based on $(HO)_3Si(CH_2)_3NHCH_2CH_2NH_2.HCl$. This is called Solution B.

Acute toxicity tests were performed on the skin and eyes of rabbits using an aqueous solution of the amine $(CH_3O)_3Si(CH_2)_3NHCH_2CH_2NH_2$, Solution A and Solution B.

The results were that the amine solution was quite irritating to both skin and eyes, Solution A was moderately so and Solution B caused little if any irritation. This lack of toxicity is an added advantage for alcohol free water solutions of type B.

The relative effectiveness of the solutions of this invention vis-a-vis the corresponding amine is shown below. In each case the composition was a mixture of 65 percent by weight powdered polypropylene and 35 percent by weight of silica having an average particle size of 6.5μ. In the blank the silica was untreated, in sample 1 the silica was treated with a 1 percent by weight aqueous solution of the above amine, in sample 2 with Solution A diluted to 1 percent by weight and in sample 3 with Solution B diluted to 1 percent by weight. In each case the silica was dried before mixing with the polypropylene.

An injection molding of each sample was made and the tensile strength of each was determined.

Table 1

| Sample | Tensile in p.s.i. |
|---|---|
| Blank | 2,994 |

Table 1-continued

| Sample | Tensile in p.s.i. |
|---|---|
| 1 | 3,453 |
| 2 | 3,549 |
| 3 | 3,400 |

EXAMPLE 5

The reaction of Example 4 was repeated using various proportions of ethylene diamine to the silane and the distribution of products between A $(CH_3O)_3Si(CH_2)_3NHCH_2CH_2NH_2.HCl$ and
B $\{(CH_3O)_3Si(CH_2)_3NHCH_2-\}_2.2HCl$ is shown in Table 2.

Table 2

| Mole Ratio of Amine/Silane | Molar Proportions of Products | |
|---|---|---|
| | A | B |
| 3 | 0.75 | 0.125 |
| 4 | 0.875 | 0.063 |
| 5 | 0.938 | 0.031 |
| 6 | 0.969 | 0.016 |

40 percent by weight solutions of mixtures of A and B were prepared and the viscosity of the solutions are shown in Table 3.

Table 3

| Mole Percent B | Viscosity at 25° C. in cps. |
|---|---|
| 5.7 | 15 |
| 9.0 | 25 |
| 12.0 | 40,000 |
| 22.0 | Gel |

EXAMPLE 6

When the following silanes are substituted in the process of Example 4, equivalent results are obtained. B is the $-NHCH_2CH_2NH_2.HCl$ group.

| Silane | Product |
|---|---|
| $(C_2H_5O)_2CH_3Si(CH_2)_3Cl$ | $(C_2H_5O)_2CH_3Si(CH_2)_3B$ |
| $(i-C_3H_7O)_2(C_2H_5)Si(CH_2)_3Cl$ | $(i-C_3H_7O)_2(C_2H_5)Si(CH_2)_3B$ |
| $(CH_3OCH_2CH_2O)_3SiCH_2Cl$ | $(CH_3OCH_2CH_2O)_3SiCH_2B$ |
| $(CH_3O)_3SiCH_2CH_2Cl$* | $(CH_3O)_3SiCH_2CH_2B$ |
| $(CH_3O)_3SiCH_2\overset{CH_3}{\underset{|}{C}}HCH_2Cl$ | $(CH_3O)_3SiCH_2\overset{CH_3}{\underset{|}{C}}HCH_2B$ |
| $(CH_3O)_3Si\overset{CH_3}{\underset{|}{C}}HCl$ | $(CH_3O)_3Si\overset{CH_3}{\underset{|}{C}}HB$ |

*Run in the absence of methanol.

EXAMPLE 7

When dimethyl amine is employed in the process of Example 2, the compound $(CH_3O)_3Si(CH_3)_3N(CH_3)_2.HCl$ is obtained.

EXAMPLE 8

Equivalent results are obtained when the procedures of Examples 2 to 4 are repeated in the absence of methanol but employing a 15 fold excess of the amine over the silane.

That which is claimed is:

1. A process for preparing the hydrochloride salt of a silyl(alkyl)amine which comprises reacting (1) a silane of the formula $(RO)_nR'_{3-n}SiR''Cl$ with at least two moles per mole of (1) of (2) a compound of the group consisting of $R'''_2NH$ and $HR'''NCH_2CH_2NR'''_2$ to form (3) $\{(RO)_nR'_{3-n}-SiR''\}_mNR'''_{3-m}$, $(RO)_nR'_{3-n}SiR''NR'''CH_2CH_2NR'''_2$ or $\{(RO)_nR'_{3-n}SiR''NR'''CH_2-\}_2$, (3) having a boiling point higher than (2) and thereafter removing unreacted (2) from the reaction zone by volatilization whereby amine hydrochlorides of the formulae $\{(RO)_nR'_{3-n}SiR''\}_mNR'''_{3-m}.HCl$, $(RO)_nR'_{3-n}SiR''NR'''CH_2-CH_2NR'''_2.HCl$ and $\{(RO)_nR'_{3-n}SiR''NR'''CH_2-\}_2.2HCl$ are obtained in which R is an alkyl or an alkoxyalkyl radical of from 1 to 4 carbon atoms,
n is 2 to 3,
R' is a lower alkyl radical,
R'' is an alkylene radical of 1 to 4 carbon atoms,
R''' is hydrogen or an alkyl radical of 1 to 8 carbon atoms R'''being hydrogen or a methyl radical when (2) is a diamine, and
m is 1 or 2.

2. The process of claim 1 in which (2) boils below 150° C. at atmospheric pressure.

3. The method of claim 1 in which (1) is 3-chloropropyltrimethoxysilane and (2) is methyl amine.

4. The method of claim 1 in which (1) is 3-chloropropyltrimethoxysilane and (2) is ethylene diamine.

5. The process of claim 1 in which the reaction is carried out in the presence of a lower aliphatic alcohol.

6. The process of claim 4 in which the reaction is carried out in the presence of a lower aliphatic alcohol.

7. The process of claim 6 in which the alcohol is methanol.

8. A stable aqueous solution made by dispersing in water the amine hydrochlorides defined in claim 1, which hydrochlorides contain less than 30 mole percent disilylalkylamine hydrochloride based on the total mono and disilylalkyl amine hydrochlorides.

9. A stable aqueous solution of claim 8 in which the disilylalkyl amine hydrochloride is present in amount less than 12 mole percent.

10. A stable aqueous solution of claim 9 in which the reactants (1) and (2) are 3-chloropropyltrimethoxysilane and ethylene diamine respectively.

11. A stable aqueous solution of claim 9 from which the alcohol has been removed.

* * * * *

UNITED STATES PATENT AND TRADEMARK OFFICE
CERTIFICATE OF CORRECTION

PATENT NO. : 4,064,155

DATED : December 20, 1977

INVENTOR(S) : John L. Speier

It is certified that error appears in the above-identified patent and that said Letters Patent are hereby corrected as shown below:

In Column 1, line 41; the line reading formula "$_nSiR''NR'''CH_{2-}\}_2$" should read "$_nSiR''NR'''CH_2-\}_2$".

In Column 1, line 44; the line "the formulae $\}(RO)_nR'_{3-n}SiR'')\}_mNR'''_{3-m} \cdot HCl.$" should read "the formulae $\{(RO)_nR'_{3-n}SiR'')\}_mNR'''_{3-m} \cdot HCl,$"

In Column 2, line 53; the word "in" should read "is".

In Column 3, line 29; the word "need" should read "needed".

In Column 3, line 59; the line reading formula "$\{(CH_3O)_3Si(CH_2)_3\}_2NH \cdot HCl$" should read "$\{(CH_3O)_3Si(CH_2)_3\}_2NH \cdot HCl$".

UNITED STATES PATENT AND TRADEMARK OFFICE
CERTIFICATE OF CORRECTION

PATENT NO. : 4,064,155

DATED : December 20, 1977

INVENTOR(S) : John L. Speier

It is certified that error appears in the above-identified patent and that said Letters Patent are hereby corrected as shown below.

In Column 4, line 3; the line reading formula "$\}(MeO)_3$" should read "$\{(MeO)_3$"

In Column 6, line 18; the line reading formula "$\{(RO)_nR'_{3-n}SiR''\}_mNR'''_{3-m'}$" should read "$\{(RO)_nR'_{3-n}SiR''\}_mNR'''_{3-m'}$"

In Column 6, line 24; the line reading formula "$(RO)_nR'_{3-n}SiR''NR'''CH_2-CH_2NR'''_2 \cdot HCl$" should read "$(RO)_nR'_{3-n}SiR''NR'''CH_2CH_2NR'''_2 \cdot HCl$"

Signed and Sealed this

Twenty-fourth Day of November 1981

[SEAL]

Attest:

Attesting Officer

GERALD J. MOSSINGHOFF

Commissioner of Patents and Trademarks